(12) United States Patent
Amouyel et al.

(10) Patent No.: US 8,114,624 B2
(45) Date of Patent: Feb. 14, 2012

(54) USE OF THE ORNITHINE TRANSCARBAMYLASE (OTC), AS A MARKER FOR DIAGNOSING BRAIN DAMAGES

(75) Inventors: Philippe Amouyel, Marcq-en-Baroeul (FR); Jean-Charles Lambert, Tourcoing (FR); Stéphanie Ferreira, Hellemmes (FR)

(73) Assignees: Genoscreen, Lille (FR); Institut National de la Sante et de la Recherche Medicale (INSERM), Paris (FR)

( * ) Notice: Subject to any disclaimer, the term of this patent is extended or adjusted under 35 U.S.C. 154(b) by 363 days.

(21) Appl. No.: 12/226,413

(22) PCT Filed: Apr. 18, 2007

(86) PCT No.: PCT/IB2007/002166
§ 371 (c)(1),
(2), (4) Date: Jan. 7, 2009

(87) PCT Pub. No.: WO2007/119179
PCT Pub. Date: Oct. 25, 2007

(65) Prior Publication Data
US 2009/0178152 A1 Jul. 9, 2009

(30) Foreign Application Priority Data

Apr. 18, 2006 (EP) .................................... 06290619

(51) Int. Cl.
*C12Q 1/40* (2006.01)
*G01N 33/53* (2006.01)
*G01N 33/542* (2006.01)
*G01N 33/537* (2006.01)
*G01N 33/566* (2006.01)

(52) U.S. Cl. ............ 435/22; 435/7.1; 435/7.9; 435/7.91; 435/7.92; 435/7.93; 436/501; 436/503

(58) Field of Classification Search .................... None
See application file for complete search history.

(56) References Cited

OTHER PUBLICATIONS

Murayama et al. "A sensitive ELISA for serum ornithine carbamoyltransferase utilizing the enhancement of immunorectivity at alkaline pH" Clinica Chimica Acta 386 125-130, 2006.
Tuchman et al. "Mutations and Polymorphisms in the Human Ornithine Transcarbamylase Gene" Human Mutation 19: 93-107, 2002.
Tuchman et al., "The molecular basis of ornithine transcarbamylase deficiency" Eur J Pediatr 159: S196-S198, 2000.
Gordon, Ornithine transcarbamylase deficiency: a urea cycle defect: European Journal of Paediatric Neurology, 7: 115-121, 2003.
Ohshita et al., "A Direct Method for the Estimation of Ornithine Carbamoyltransferase Activity in Serum" Clinica Chimica Acta, 67: 145-152, 1976.
Azevedo et al. "New polymorphic sites within ornithine transcarbamylase gene: population genetics studies and implications for diagnosis" Molecular Genetics and Metabolism 78: 152-157, 2003.
Loring et al., "A Gene Expression Profile of Alzheimer's Disease" DNA and Cell Biology, 20: 683-695, 2001.
Kamboh, M. Llyas, "Molecular Genetics of Late-Onset Alzheimer's Disease" Annals of Human Genetics 68, 384-404, 2004.
Butterworth, Roger F. "Evidence for Forebrain Cholinergic Neuronal Loss in Congenital Ornithine Transcarbamylase Deficiency" Metabolic brain Disease, 15: 83-91, 2000.
Ishikawa et al., "A novel method for measuring serum orithine carbamoyltransferase" The Association of Clinical Biochemists 40: 264-268, 2003.
NT_079573, *Homo sapiens* chromosome X genomic conig, reference assembly, and International Human Genome Sequencing Consortium, Finishing the euchromatic sequence of the human genome, Nature : 931-945, 2004.

*Primary Examiner* — Olga N Chernyshev
(74) *Attorney, Agent, or Firm* — Morgan, Lewis & Bockius LLP

(57) ABSTRACT

The present invention pertains to the domain of brain diseases, and provides novel markers and methods for diagnosing a brain alteration in an individual, especially in patients suffering from neurodegenerative diseases such as Alzheimer's disease. The present invention also provides tools for evaluating the probability, for an individual, of developing the disease, as well as a target for identifying new drugs for treating neurodegenerative diseases such as Alzheimer's disease. In particular, the invention provides a genetic marker based on combination of two single nucleotide polymorphism, at positions −389 and −241 of the ornithine transcarbamylase (OTC) gene.

10 Claims, 3 Drawing Sheets

(a)

(b)

Figure 1:
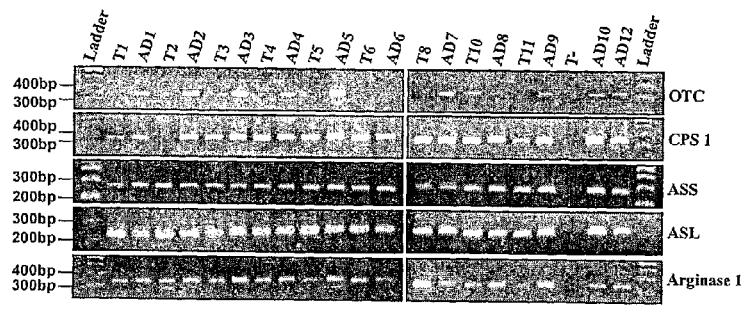

|  | -544 G/A | -389 G/A | -260 C/G | -241 A/G | Lys46Arg |
|---|---|---|---|---|---|
| -544 G/A | - | | | | |
| -389 A/G | 0.97 | - | | | |
| -260 C/G | 0.99 | 0.96 | - | | |
| -241 A/G | 0.92 | 0.94 | 0.97 | - | |
| Lys46Arg | 0.90 | 0.97 | 0.99 | 0.97 | - | ns
USE OF THE ORNITHINE TRANSCARBAMYLASE (OTC), AS A MARKER FOR DIAGNOSING BRAIN DAMAGES

RELATED APPLICATIONS

The present application is a U.S. National Phase Application of International Application No. PCT/IB2007/002166, filed Apr. 18, 2007, which claims priority to European Patent Application 06290619.3, filed Apr. 18, 2006, all of which are hereby incorporated by reference in their entirety.

SEQUENCE LISTING SUBMISSION VIA EFS-WEB

A computer readable text file, entitled "045636-5097-US-SubstituteSequenceListing.txt," created on or about Jun. 10, 2011, with a file size of about 9 kb contains the sequence listing for this application and is hereby incorporated by reference in its entirety.

The present invention pertains to the domain of brain diseases, and provides novel markers and methods for diagnosing a brain alteration in an individual, especially in patients suffering from neurodegenerative diseases such as Alzheimer's disease. The present invention also provides tools for evaluating the probability, for an individual, of developing the disease, as well as a target for identifying new drugs for treating neurodegenerative diseases such as Alzheimer's disease.

Alzheimer's disease (AD) is a complex multifactorial neurodegenerative disease and a leading cause of dementia among elderly people. About 5% of the people aged 65 or above are affected with AD and the prevalence rises steeply to 19% after age 75 and to 47% after age 85. Currently, there are more than 4 millions of AD cases in the U.S., 850,000 in France and 12-14 millions worldwide. The 85 and older group, in which almost 50% is affected by some form of dementia, is one of the fastest growing segments of the European and American populations. However, modelisation suggests that a 5-year delay could reduce dementia prevalence by 50%, allowing a potential control of this dramatic pandemia. Such a possibility raises 2 essential issues: (i) early diagnosis and (ii) efficacy of therapeutics.

To date, although important improvements have been realised, it is still difficult to set a diagnosis at the very early stage of the disease. Furthermore, there is no curative treatment even if some symptomatic treatments of cognitive functions are available, mainly acetylcholinesterase inhibitors (3 molecules currently registered) and more recently, an antagonist of the NMDA receptor. However, this entire therapeutic arsenal, when patients can benefit from it, allows at best a delay in the inevitable dependency resulting from the disease aggravation.

As a consequence, early diagnosis and therapeutic arsenal are closely linked. In order to propose an effective treatment, it appears essential to establish a diagnosis at the earliest stage of the disease, or even to detect the first signs of the pathology at an infra-clinic level.

In subjects growing old, memory and cognitive complaints are usually observed but are not necessarily associated with a pathological cognitive decline. These complaints can be a mere indicator of an isolated and minor trouble or, to the contrary, indicate an objective cognitive and pathological alteration. Within this framework, the concept of "mild cognitive impairment" or MCI was proposed to characterize the subjects located in the zone of transition between normal ageing and dementia. These patients present an objective decline of their cognitive performances without fulfilling the clinical criteria of dementia. The conversion rate of these patients is about 14% a year, and 50% of the MCI cases will have developed dementia three years later. Very few works make it possible to have a longer term vision, but a non negligible part of these MCI cases will not develop dementia (approximately 20% 5 years later).

Despite their frequency, the molecular genetic basis of neurodegenerative diseases is unclear. Concerning Alzheimer's disease, it is established that there are two types of AD: (i) familial AD (FAD), which runs in families, and (ii) sporadic AD, in which no obvious family history is present. Familial early-onset forms of AD account for less than 5% of the total number of cases and these have been linked to mutations in three different genes: the amyloïd precursor protein (APP) gene on chromosome 21, the presenilin 1 (PS1) gene on chromosome 14 and the presenilin 2 (PS2) gene on chromosome 1 (Cruts and Van Broeckhoven, 1998). The aetiology of late-onset sporadic AD is more complex with the possible involvement of, and interaction between, environmental factors and numerous genes. Apolipoprotein E (APOE), especially the APOE ε4 allele, has been established as a strong susceptibility marker that accounts for approximately 20% of the genetic risk in late-onset AD (Kamboh, 2004). However, as the APOE ε4 allele is neither necessary nor sufficient alone for the development of AD, it is likely that other genetic and/or environmental factors, which act alone or in conjunction with APOE ε4, can modify the risk of AD. Recently, genome-wide linkage or linkage disequilibrium studies (LD) on late-onset AD have provided evidence for the existence of multiple putative genes for AD on several chromosomes. However, the general location of putative AD genes on a given chromosome covers a broad region. Furthermore, one of these regions may also contain several genes of interest. It is therefore not clear whether these findings indicate the existence of multiple genes within a chromosome, or if they represent chance variation within the region of interest, because estimates of location of genes based on linkage studies can vary by 30 cM or more for complex disorders (Roberts et al., 1999).

In order to prioritise the selection of candidate genes located within these regions of interest, an appropriate and robust method would be to combine the genetic map information data with the gene expression profiling data for the rapid identification of genes. This assumption results from two major observations:

(i) the expression of numerous genes is modified during AD aetiology (Blalock et al., 2004; Brown et al., 2002; Colangelo et al., 2002; Li et al., 2003; Loring et al., 2001);

(ii) as well as qualitative variations (i.e., coding mutations) in genes already involved in AD, quantitative variations in the expression of these same genes have also been shown to be genetic determinants of disease. For example, functional polymorphisms within the promoter sequences of APOE, PS1 and PS2 genes have been associated with increased risk of developing AD (Lambert et al., 2002; Riazanskaia et al., 2002; Theuns et al., 2000). A similar involvement of APP has been discussed (Lahiri et al., 2005).

Consequently, the inventors made the hypothesis that genes exhibiting a differential expression between patients and controls, and located in one of the regions of interest defined by previous genome scans, could constitute potential candidate genes for AD. In order to develop the 'genomic convergence' approach, they developed a home-made microarray to screen 2741 Open Reading Frames (ORFs) contained in the risk-associated loci (over nine different chromosomes) previously identified in genome scan studies (Lambert et al., 2003). This expression profiling from brain tissues in 12 controls and 12 patients with AD lead them to select 106 differentially expressed genes. Among these 106 modulated genes, 11 were located on chromosome X.

Surprisingly, the inventors found that one of these genes is strongly over-expressed in the brain of AD cases, whereas it is not expressed in the brain of controls. This gene is the Ornithine TransCarbamylase (OTC) gene located at Xp21.1. OTC is a key enzyme of the urea cycle, which is not functional in the 'normal brain' (Felipo and Butterworth, 2002; Wiesinger, 2001).

In healthy subjects, OTC is expressed almost exclusively in hepatocellular mitochondria and regarded as a liver-specific marker. The serum level of this protein was shown to be increased in patients with hepatic disorders like hepatitis, cirrhosis and cancer. Although not expressed in the brain of healthy subjects, deficiency in this enzyme can lead to neurological disorders. Indeed, one of the usual symptoms of ornithine transcarbalylase deficiency (which is very heterogeneous in its presentation), is hyperammonaemic coma (Gordon, 2003).

The inventors extensively studied the OTC gene in AD and control individuals. They have also studied the level of OTC activity present in the cerebrospinal fluid from subjects suffering from MCI, AD and non-AD dementia, and their results, disclosed in the experimental part below, demonstrate that the OTC gene, as well as OTC expression in the brain, are relevant susceptibility and/or diagnosis markers for Alzheimer's disease and other brain pathologies.

A first aspect of the present invention is a method for in vitro diagnosing a brain alteration in an individual, comprising a step of detecting (and/or quantifying) ornithine transcarbamylase (OTC) in a sample of cerebrospinal fluid from said individual. In the context of the present invention, a "brain alteration" designates any kind of brain neurodegeneration, and especially dementia.

A particular interest of the method according to the present invention is that it enables the diagnosis or detection of a brain alteration at very early stages of a brain disease, and even at an infra-clinic level, i.e., before the appearance of clear symptoms of said disease (having regard to the cognitive abilities and the behaviour of the subject).

When performing the method according to the invention, the physician will be able, in certain clinical contexts, to diagnose a neurodegenerative disease, or, more precisely, to establish a diagnosis of Alzheimer's disease or of a non-AD dementia. By "non-AD dementia" is meant any kind of dementia which is not caused by Alzheimer's disease. As non-limitative examples of such dementia, the following can be cited: vascular dementia, mixed dementia, fronto-temporal dementia, dementia with Lewy body etc.

The method according to the invention can advantageously be performed on subjects who suffer from a mild cognitive impairment (MCI), since this enables the objective diagnosis of a pathology, in subjects in whom it is a priori difficult to determine whether their cognitive complaints correspond to a minor trouble or to a real and possibly progressive pathology.

To perform the method according to the invention, a variety of techniques can be used for detecting the ornithine transcarbamylase (OTC) and, advantageously, measuring its level in the cerebrospinal fluid:

According to a first technique, the presence of OTC in the sample of cerebrospinal fluid is determined by detecting the OTC activity. A quantitative measure of OTC activity also enables the quantification of OTC. Assays which can be used to detect OTC activity are described below and in the scientific literature (Ishikawa et al., 2003; Ohshita et al., 1976). In a preferred embodiment, the OTC activity is detected by measuring the production of citrulline produced after addition of carbamyl phosphate and ornithine to said sample. Advantageously, carbamyl phosphate and ornithine, which are the substrates of OTC, are added in excess to the sample, and the production of citrulline is measured during a determined time. The production of citrulline can be measured by a calorimetric assay, for example by using a diacetylmonoxime-thiosemicarbazide reaction without deproteinization, as described in Ohshita, Takeda et al. (1976).

A second technique which can advantageously be used in the methods of the invention consists of measuring the OTC activity through an assay based on the reverse reaction of ornithine transcarbamylase, as described by Ishikawa et al. (Ishikawa et al., 2003). Briefly, a conversion of ornithine into glutamate, though the actions of OKT, P5CDH and GDH, forces the OCT to catalyse its reverse reaction (conversion of citrulline to ornithine), so that 3 mol of glutamate are produced from 1 mol of substrate citrulline. The glutamate is then measured by glutamate oxydase and Trinder's reagent. A preliminary reaction can be performed to avoid interference with the endogenous glutamate.

A third technique is based on an immunoassay with a monoclonal or polyclonal antibody directed against OTC. An example of immunoassay that can be performed is an ELISA assay with monoclonal antibodies obtained against purified recombinant OTC, such as described by Murayama et al. (Murayama et al., 2006). The skilled artisan can also use other assays, such as ELISA or Western blots with monoclonal or polyclonal antibodies directed against OTC or a fragment thereof. For example, a monoclonal or a polyclonal antibody obtained against a polypeptide specific of the human OTC, such as the polypeptide MKTAKVAASDWTFLHCLPRK (SEQ ID No: 17), can be used. Other fragments of the human OTC may also be used in the context of the invention. Said technique permits the detection and/or the quantification of OTC.

In the above methods, a brain alteration is diagnosed when a significant level and/or activity of ornithine transcarbamylase is detected in the cerebrospinal fluid. By "significant level or activity" is meant a level or activity of ornithine transcarbamylase which is higher than the level or activity which is statistically observed in healthy subjects. This brain alteration is indicative of a brain disease, either already declared or still at an infra-clinic level.

A second aspect of the present invention pertains to the use of the ornithine transcarbamylase (OTC) gene, as a genetic marker for determining the genetic predisposition of an individual to a brain disease such as Alzheimer's disease.

In particular, the invention concerns a method for in vitro predicting an increased risk, for an individual, of developing a brain disease, or for in vitro diagnosing a brain disease in an individual, comprising a step of genotyping the region controlling the expression of the ornithine transcarbamylase (OTC) gene in a biological sample from said individual. This method is particularly appropriate for predicting an increased risk or for in vitro diagnosing a neurodegenerative disease, especially Alzheimer's disease. Of course, the new genetic marker described herein can be combined to other markers, such as, for example, the apolipoprotein E gene, in order to increase the statistical significance of the test.

In a preferred embodiment of this method, the −389 A/G and −241 G/A SNPs (single nucleotide polymorphisms) are analyzed.

This analysis can be performed through the amplification of one or two fragments of the region controlling the expression of the ornithine transcarbamylase (OTC) gene. If two fragments are amplified, one of them comprises the −389 nucleotide, and the other comprises the −241 nucleotide. If only one fragment is amplified, it is chosen so as to embrace both the −389 and −241 nucleotides. In a proposed embodiment of the methods according to the invention, illustrated in the experimental part below, a polymerase chain reaction is performed with the primers CTCCTGAGGTGGCCAT-AGTTG (SEQ ID No:1) and CCAACATGGTGAATC-CCCGTC (SEQ ID No:2).

The genotyping of the −389 A/G and −241 G/A polymorphisms can also comprise a step of analysing enzymatic restriction patterns of the amplification product(s). For example, the genotyping of the −389 A/G polymorphism can comprise a restriction of the amplification product by AlwNI, and the genotyping of the −241 G/A polymorphism can comprise a restriction of an amplification product by HinI. The patterns obtained in each case are specified in the experimental part below.

The methods according to the invention advantageously comprise an interpretation step, in which the $G_{-389}$-$G_{-241}$ haplotype is indicative of a decreased risk of developing Alzheimer's disease, and the $A_{-389}$-$A_{-241}$, haplotype is indicative of an increased risk of developing Alzheimer's disease.

The invention also concerns a method for diagnosing a brain alteration in a deceased individual, comprising a step of labelling a brain biopsy from said individual, with an anti-OTC antibody, which can be a monoclonal or polyclonal antibody obtained against a polypeptide specific of the human OTC. The presence of ornithine transcarbamylase in cerebrovascular endothelial cells is indicative of a brain alteration. In particular, the presence of OTC in cerebrovascular endothelial cells can be indicative of Alzheimer's disease.

According to the present invention, an antibody directed against human ornithine transcarbamylase can hence be used for the in vitro diagnosis of a brain disease, such as a mild cognitive impairment, Alzheimer's disease, or a non-Alzheimer's disease dementia, either in a deceased or in a living subject. An example of antibody which can be used in the methods according to the invention is a polyclonal antibody obtained against the polypeptide MKTAKVAASDWTFLH-CLPRK (SEQ ID No: 17).

The present invention also pertains to a screening method for identifying compounds able to prevent, alleviate or treat Alzheimer's disease and/or other brain diseases, comprising a step of identifying compounds which modulate the expression and/or the activity of the ornithine transcarbamylase in cells. Depending on several factors, which include the nature and the stage of the disease, the ammonia concentration in the cerebrospinal fluid, etc., it is preferable either to increase, or to decrease the activity of the ornithine transcarbamylase. Therefore, in the above screening method, the term "modulate" means "activate" as well as "inhibit".

In a preferred embodiment of the screening method according to the invention, the ability of compounds to modulate the expression and/or the activity of the ornithine transcarbamylase is assayed in cultured vascular endothelial cells which express the OTC gene.

The same techniques as described above for measuring the OTC expression and/or activity in the cerebrospinal fluid of patients can be used to perform the screening methods according to the invention. However, it can be noted that the technique consisting of measuring the OTC activity through an assay based on the reverse reaction of OTC, as described by Ishikawa et al. (Ishikawa et al., 2003), can be automated and is hence particularly suitable for high-throughput screening. Of course, for screening compounds to identify modulators of the OTC, the OTC expression and/or activity is measured in the presence and in the absence of the candidate compounds, and the obtained results are compared.

Other objects of the present invention are kits for performing the above-described methods. Such a kit, when designed for measuring the OTC activity or OTC quantity (either in cerebrospinal fluid for establishing a diagnosis, or in medium in the case of a screening method), comprises at least a solution of ornithine and a solution of carbamyl phosphate, and, optionally, a solution of triethanolamine and/or a solution of phosphoric acid and sulphuric acid, and/or a solution of butanedione.

Alternatively or complementarily, a kit for diagnosing a brain disease or for screening molecules, according to the present invention, comprises at least an antibody directed against human ornithine transcarbamylase, for example a monoclonal or a polyclonal antibody directed against the polypeptide MKTAKVAASDWTFLHCLPRK (SEQ ID No: 17).

According to another embodiment, a kit according to the invention, designed for diagnosing a brain disease or for predicting a risk, for an individual, of developing such a disease, comprises at least a set of primers for amplifying the region controlling the expression of the ornithine transcarbamylase (OTC) gene comprising the −389 and −241 nucleotides. This kit can also comprise, in addition, AlwNI and HinI restriction enzymes.

Each kit according to the present invention can also comprise a notice of use, which indicates the steps of the method(s) that can be performed with said kit, the nature of the information that can be obtained and, possibly, how this information should be interpreted (depending on the context). Positive and negative controls, including, for example, recombinant OTC, can also be included.

The present invention also concerns a transgenic non-human mammal which carries an expression cassette for expressing OTC in a conditional and/or tissue-specific manner. Such an animal can be used as a model of Alzheimer's disease. In a preferred embodiment of a transgenic animal according to the invention, the expression of the OTC transgene is dependent on the activity of an inducible transcriptional activator. For example, the OTC transgene can be under the control of a tetracycline-responsive promoter element (TRE). An example of inducible transcriptional activator that can be used to obtain a transgenic animal according to the invention is a tetracycline-controlled transactivator protein (tTA), which will preferably be expressed under the control of a tissue-specific promoter. A particularly suitable promoter for driving the expression of this transcriptional activator is the vascular endothelial cadherin promoter.

The invention is further illustrated by the following figures and examples.

LEGENDS TO THE FIGURES

FIG. 1: Expression of the enzymes of the urea cycle in the brain. RT-PCR experiments. Total RNA was extracted from the brain of 11 AD cases (AD) and 9 controls (T) used for the transcriptomic analysis. A control was done by omitting the RNA sample (T−); carbamoyl-phosphate synthetase 1 (CPS1), ornithine transcarbamylase (OTC), argininosuccinate synthetase 1 (ASS), argininosuccinate lyase (ASL)

Figure 2:
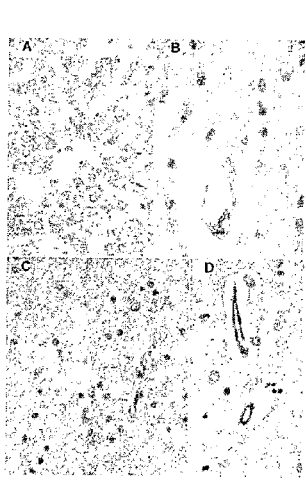

FIG. 2: Immunohistochemistry experiments. The cytoplasm of normal hepatocytes is intensely stained brown by the anti-OTC antiserum, as shown on pannel A, but not the vessels and the intrahepatic bile ducts. The cortex of the control brain is not immunoreactive for OTC (B), whereas the endothelium of the brain cortex is labelled by this antibody in 6 out of 12 Alzheimer patients (C and D).

Figure 3:
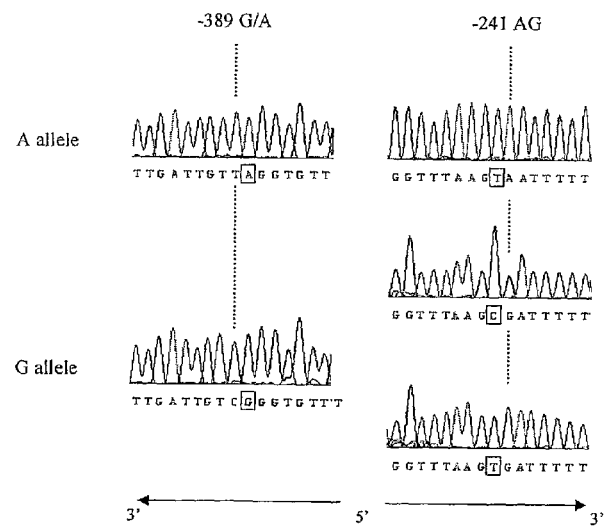

FIG. 3: Representative electrophoregram of methylation status of the OTC promoter at position −389 and −241 by bisulfite sequencing. The box indicated the absence (A) or presence (C) of methylation accordingly to the −389 SNP allele.

Figure 4:
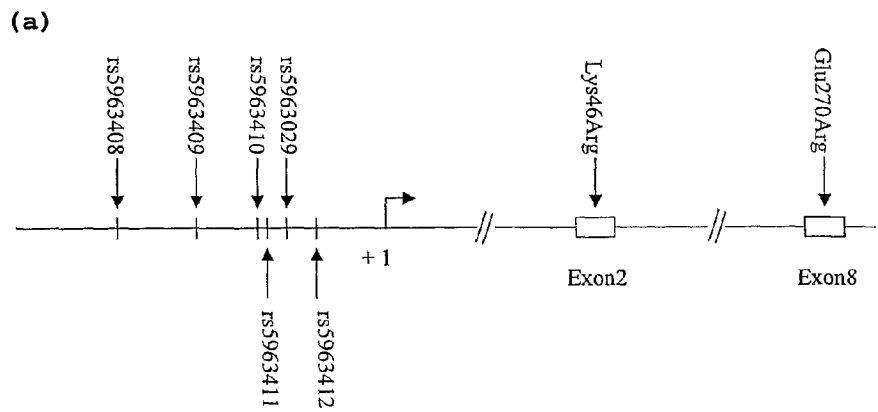

FIG. 4: (a) genetic localisation of the OTC SNPs. (b) estimation of linkage disequilibrium between the different SNPs.

Figure 5:
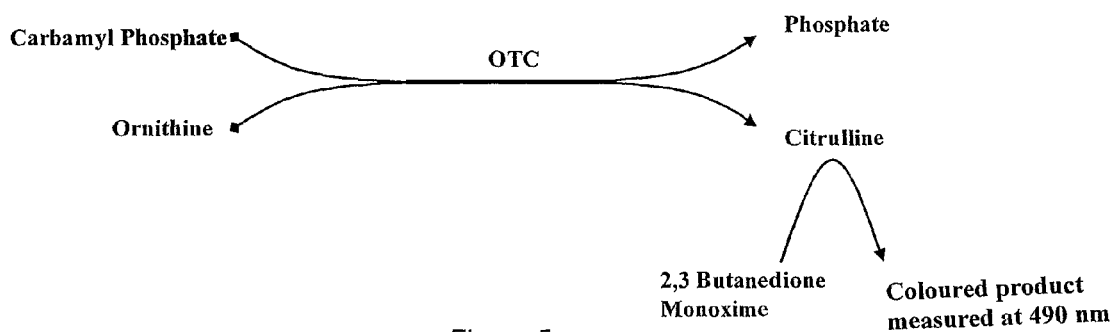

FIG. 5: Schematic representation of the reaction catalyzed by the OTC.

Figure 6:
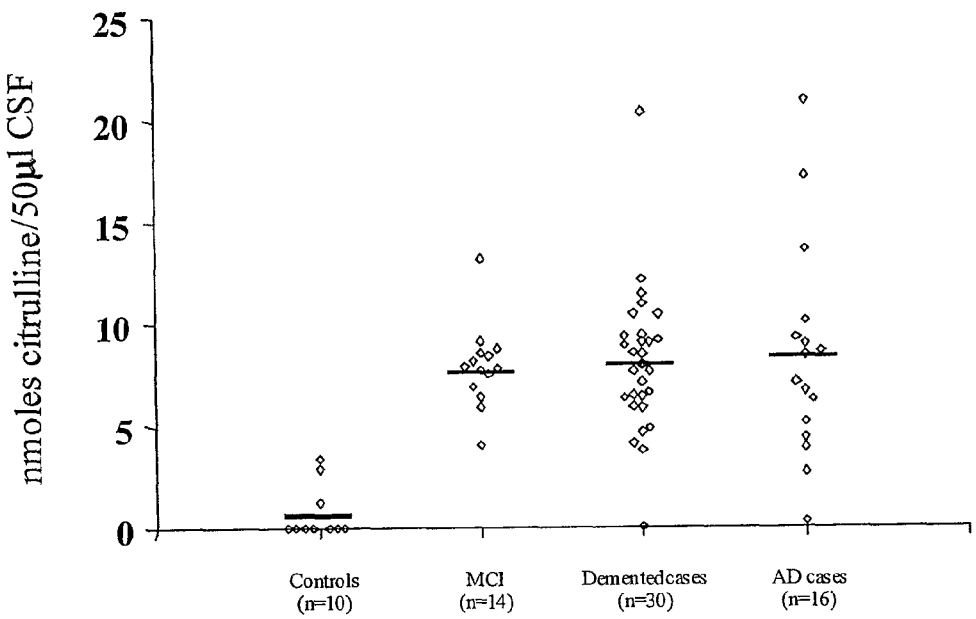

FIG. 6: Quantification of the de novo produced citrulline corresponding to the activity of the OTC measured in 30 minutes, in 50 μl of CSF, in controls (n=10), MCI subjects (n=14), AD cases (n=16) and non-AD dementia cases (n=30).

Figure 7:
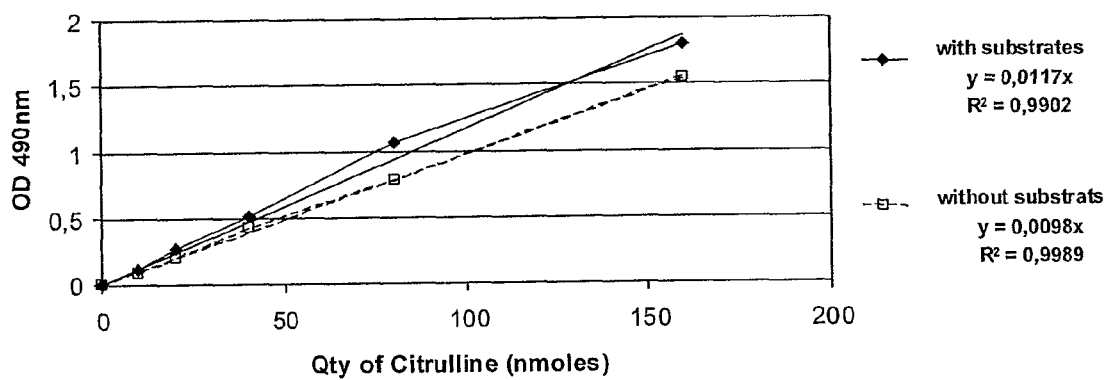

FIG. 7: Citrulline measurement in presence or absence of OTC substrates.

Figure 8:
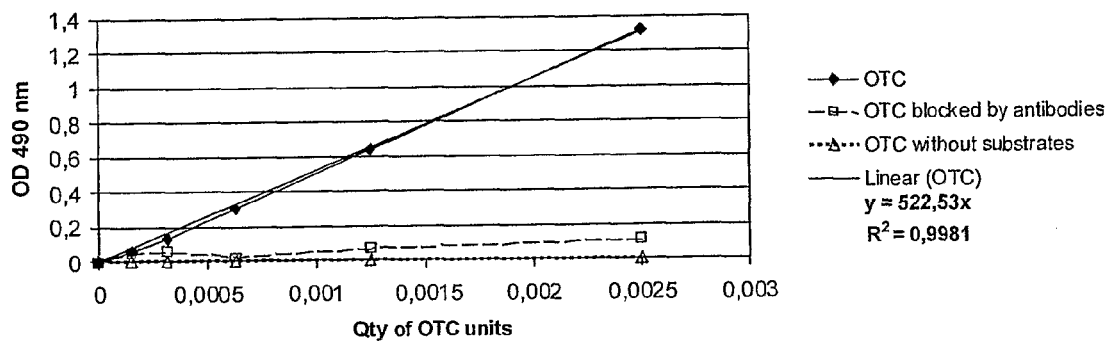

FIG. 8: Enzymatic measure of OTC activity and control tests.

EXAMPLES

Example 1

Identification of the OTC Gene, as a Potential Genetic Marker for Alzheimer's Disease 1.1. Materials and Methods Brain samples. Brains were obtained at autopsy from 114 patients with early- and late-onset sporadic AD accessioned from the Greater Manchester region of United Kingdom during years 1986-2001 (mean age at death=73.1±9.1 years old; mean age at onset=65.9±10.3 years old; 51% male). All patients were of Caucasian ethnic origin. Pathological diagnoses were made in accordance with CERAD Neuropathological Criteria for AD (Mirra et al., 1991). All patients were at Braak stages 5 or 6 at time of death. Control brains were obtained from an initial set of 167 brains obtained from routine autopsies carried out at the Hospices Civils de Strasbourg (France). Recruitment was designed to exclude cases of dementia (individuals were not recruited from medical institutions where the majority of patients presented with dementia, but from a general hospital). Most cases were admitted less than 48 hours before death via emergency services and were living at home prior to their admission. Cases referred to autopsy for neurological pathologies were excluded. Neuropathological criteria were applied to define Braak stages (Braak and Braak, 1991) or in accordance with CERAD Neuropathological Criteria (Mirra et al., 1991). Again, all control subjects were Caucasian.

Total RNA was extracted from frozen frontal cortex brain tissue from all 114 AD and 167 control samples using phenol/chloroform protocol (TRIzol®) reagent, Invitrogen). The quality of total RNA was assessed using Agilent 2100 bionalyser and the ratio of ribosomal RNA 28S/18S systematically estimated using the Agilent 2100 bionalyser bio-sizing software. Twelve AD cases and 12 controls were selected from the initial samples according to criteria: (i) a ratio of ribosomal RNA 28S/18S greater than or equal to 1.0; (ii) a Braak stage below 2 for the control samples. The main characteristics of the samples are shown in Table 1 below.

TABLE 1

Main characteristics of the brain samples used for transcriptomic analyses.

| AD Case | Gender | Age at death (y) | 28S/18S Ratio | Control case | Gender | Age at death (y) | 28S/18S Ratio |
|---|---|---|---|---|---|---|---|
| AD1 | F | 68 | 1.4 | T1 | F | 74 | 1.0 |
| AD2 | M | 86 | 1.0 | T2 | F | 72 | 1.2 |
| AD3 | M | 67 | 1.9 | T3 | M | 75 | 1.0 |
| AD4 | F | 66 | 1.6 | T4 | F | 74 | 1.7 |
| AD5 | M | 66 | 1.4 | T5 | F | 70 | 1.1 |
| AD6 | F | 84 | 1.7 | T6 | M | 67 | 1.4 |
| AD7 | M | 77 | 1.1 | T7 | M | 69 | 1.8 |
| AD8 | M | 71 | 1.2 | T8 | F | 73 | 1.4 |
| AD9 | M | 65 | 1.3 | T9 | F | 80 | 1.1 |
| AD10 | F | 64 | 1.0 | T10 | M | 72 | 1.2 |
| AD11 | F | 85 | 1.0 | T11 | M | 78 | 1.2 |
| AD12 | F | 77 | 1.3 | T12 | M | 70 | 1.5 |
|  | 50% | 73.0 ± 8.4 | 1.3 ± 0.3 |  | 50% | 72.8 ± 3.7 | 1.3 ± 0.3 |

Microarray analyses. Specific oligonucleotides for 2741 open reading frames located within the regions of interest defined by genome scan studies were designed using the OLIGOMER software (Mediagen). The main criteria of selection were: (i) a length of 60 oligonucleotides; (ii) the hybridization temperature (between 65 and 75° C.); (iii) the specificity of the oligonucleotide sequence; (iv) inability to form a secondary structure at the hybridization temperature; (v) an oligonucléotide sequence close to the 3'-UTR end of the selected ORF. After synthesis of the oligonucleotides, these were systematically purified in order to obtain a population homogeneous in length (Sigma). All the oligonucleotides were functionalised with a $C_6H_{12}NH2$ arm at their 5' end.

The genetic expression of each AD case was compared with a pool of control samples in order to decrease potential inter-individual variability in the control population. cRNAs—representative of the initial mRNA population from 10 ug of total RNA—was produced by amplification and labeled by Cy5 or Cy3 fluorophores using the Agilent Fluorescent Linear Amplification Kit as described by the supplier. A dye-swap strategy was followed, with each AD sample being analyzed on two independent microarrays on which the same sample was labeled either by Cy3 or Cy5 fluorophores. For hybridization, 4 µl of cRNA from each AD case was mixed with 4 µl of cRNA from the control pool. This mix was then dissolved in 22 µl of hybridization buffer (Supplier) to obtain a final concentration of 40% formamide, 2.5×Denhardt's, 0.5% SDS and 4×SSC (Sambrook and Russel 2001). After incubating at 95° C. for 5 min, the mix was applied to the slides under a cover slip. The slides were then placed in a hybridisation chamber (Corning), and 30 µl of hybridisation buffer was added to the chamber before sealing. The sealed chambers were incubated for 14-16 h in a water bath at 42° C. The slides were then washed twice in SSC 2× and SDS 0.1% for 5 min at 42° C., once for one min in SSC 0.2× at room temperature and then once for 1 min in SSC 0.1× at room temperature. Finally, the slides were dried by centrifugation at 1000 rpm for 5 min at room temperature. After hybridisation, arrays were scanned using an Affymetrix 418 scanner and images were processed using ImaGene 6.0 (Biodiscovery) software. Raw data was then analysed using the LIMMA library (Linear Models for Microarray Data) (Smyth et al., 2003) running under the statistical language R v2.0.1 (Ihaka and Gentlman, 1996). A normalisation protocol, consisting of a within-array print-tip less normalisation to correct for dye and special effects (Yang et al., 2002), was applied on the background subtracted median intensities of the unflagged spots. After normalization, identification of statistically significant regulation was performed using moderated t-statistic with empirical Bayes shrinkage of the standard errors (Lönnstedt and Speed, 2002).

RT-PCR. Reverse-transcription was performed from 500 ng of total RNA extracted from frontal cortex of 11 AD cases and 9 controls initially used for the microarray experiments. Specific amplification of mRNAs from the carbamoyl-phosphate synthetase 1 (CPS1), ornithine transcarbamylase (OTC), argininosuccinate synthetase 1 (ASS), argininosuccinate lyase (ASL) and arginase 1 genes was obtained using oligonucleotide sets described in Table 2. Primers were designed within different exons in order to avoid potential contamination by amplification of genomic DNA. Control experiments were performed by omitting RNA sample. The PCR products were analysed on agarose gels (3%).

TABLE 2 sets of oligonucleotides used for a specific RT-PCR detection of the expression of the genes coding for the urea cycle enzymes

| | | sequence | SEQ ID No: | Length (bp) |
|---|---|---|---|---|
| CPS I | forward | aagacctggcatcaggctcc | 18 | 344 |
| | reverse | tggtagccagccagtggttg | 19 | |
| OTC | forward | tcccaattatcaatgggctg | 20 | 319 |
| | reverse | catgcttatccaaagtgtctg | 21 | |
| ASS | forward | cagtcctgctctgccgcctg | 22 | 270 |
| | reverse | ccggccagatgaactcctcca | 23 | |
| ASL | forward | gaggaaccgcccaacatg | 24 | 226 |
| | reverse | ccaccttgtctaggccatgg | 25 | |
| Arginase I | forward | cctacagtattgagaaaggc | 26 | 334 |
| | reverse | ttccacttgtggttgtcagt | 27 | |

Immuno-histochemistry experiments. Anti-peptide polyclonal antibodies (pAbs) against a 20 a.a. polypeptide, specific of the human OTC protein (MKTAKVAASDWTFLH-CLPRK (SEQ ID NO: 28)), were developed from a standard protocol (immunization of three months, Proteogenix SA, France). Brain tissue samples were obtained at autopsy from 12 Alzheimer patients (7 men and 5 women, ranging from 57 to 95 yrs; mean age 75.3 yrs) and 4 controls (patients devoid of any neurological disease, in whom the neuropathological study didn't show any Alzheimer pathology, mean age 69.5 yrs). All the patients were prospectively followed in the University hospital of Lille. One half of the brain was fixed in formalin for light microscopy examination, the other part of the brain was frozen for biochemical study. In all patients, the Alzheimer pathology was confirmed by immunohistochemistry and western blot analysis of Tau, Aβ and α-synuclein (Delacourte et al., 2002).

Paraffin sections from the anterior frontal cortex (BA 10) were processed in a Benchmark-XT automate (Ventana, Tucson, Ariz., USA). The anti OTC antibody and the pre-immune rabbit serum (both diluted 1/500) were applied after heating, and revealed by a standard immunoperoxidase technique. Positive controls were paraffin sections of formalin-fixed liver. Negative controls were brain sections from the Alzheimer patients and controls, processed with a pre-immune rabbit serum.

Genotyping. Genotyping of 8 SNPs was determined by enzymatic digestion following PCR amplification (Table 3 below). Fifty percent of the genotypes were randomly performed twice and no discrepancy was observed.

TABLE 3 sets of oligonucleotides used for the genotyping of the OTC SNPs.

| SNP | position | Reference | primers | SEQ ID No | Enzyme |
|---|---|---|---|---|---|
| 1 | −544 | rs5963408 | ctcctgaggtggccatagttg | 1 | Alu I |
| 2 | −389 | rs5963409 | | | AlwN I |
| 3 | −260 | rs5963410 | ccaacatggtgaatccccgtc | 2 | Mnl I |
| 4 | −241 | rs5963411 | | | Hin I |
| 5 | −146 | rs5963029 | atctgggctcactgcaacct | 3 | Bst5F I |
| | | | gagaccagcctggccaacag | 4 | |
| 6 | −69 | rs5963412 | gtggagacggggattcaccat | 5 | HpyCH4 III |
| | | | gggcacggtggctcacgact | 6 | |
| 7 | Lys46Arg | rs1800321 | gtgtggacaaccactacaaa | 7 | DdeI |
| | | | tgttacatacctctccttc | 8 | |
| 8 | Glu270Arg | rs1800328 | atggtaccaagctgttgctg | 9 | Alw26I |
| | | | cgcttttcttctcctcgtc | 10 | |

For determining the nucleotide present at position −389, the 718 bp amplification product obtained after amplification with the primers of SEQ ID Nos: 1 and 2 is digested AlwN I, and the pattern is interpreted as follows: if the nucleotide at position −389 is G, then the amplification product is not restricted, whereas the digestion results in two bands (of 471 and 247 bp) if the nucleotide at position −389 is A.

For determining the nucleotide present at position −241, the 718 bp amplification product obtained after amplification with the primers of SEQ ID Nos: 1 and 2 is digested Hin I, and the pattern is interpreted as follows: if the nucleotide at position −241 is A, then the amplification product is restricted into 4 fragments (of 340, 226, 138 and 14 bp), whereas a G at position −241 creates an additional Hin I restriction site, so that the digestion results in five fragments (of 340, 137, 89, 138 and 14 bp).

Methylation status at position −389 and −241. In order to determine the methylation status of the cytosines of the CpG motifs at position −389 and −241 within the human OTC promoter, treatment of genomic DNA by bisulfite was performed using the CpGenome DNA Modification Kit (Chemicon). Briefly, one µg of genomic DNA extracted from peripheral blood lymphocytes was treated with sodium bisulfite and hydroquinone and incubated at 50° C. for 16 hours. Following this treatment, unmethylated cytosines were converted to uracil and methylated cytosines remained unchanged. After purification, the bisulfite-modified DNA was immediately used for PCR or stored at −70° C.

Bisulfite-modified DNA (20 ng) was used as template for PCR in order to determine the methylation status of the CpG/A motif at position −389 using the primer se: 5'-ATAAATGTGAAGTTGTAGAT-5' (SEQ ID No: 11) and 5'-TAATTACCTATTAATTCTAAC-3' (SEQ ID No: 12). The amplification product was next re-amplified using the primer set: 5'-GAATAGGTTGTTAGGGGAAG-3' (SEQ ID No: 13) and 5'-ATAAATGTGAAGTTGTAGAT-3' (SEQ ID No: 14). Bisulfite-modified DNA (20 ng) was used as template for PCR in order to determine the methylation status of the CpG/A motif at position −241 using the primer set: 5'-TGGGTTTATTGTAATTTTTGTTTTTT-3' (SEQ ID No: 15) and 5'-CTAACCAACATAATAAATCCCCCATC-3' (SEQ ID No: 16). The PCR fragments from individuals bearing either the GG or AA genotypes (4 individuals by genotype) for both OTC promoter SNPs were cloned into a pGEM-T Easy Vector (Promega) and at least 5 clones with appropriate sized inserts were sequenced for each individual.

AD case-control study. The French AD and control samples were Caucasian (AD cases n=600, age=72.4±7.2 years, age at onset=69.5±7.4 years, 39.5% male; controls n=664, age=72.5±7.9 years, 36% male). An early age at onset was defined as $\leq 65$ years. A diagnosis of probable AD was established according to DSM-III-R and NINCDS-ADRDA criteria. Caucasian controls were recruited and defined as subjects without DMS-III-R dementia criteria, with integrity of cognitive function and with a MMS score $\geq 25$. Presence of family history of dementia was an exclusion criterion. Controls were recruited in retirement homes or from electoral rolls (altruistic volunteers). Each individual or next of kin gave informed consent.

Statistical analysis. The SAS software, release 8.0, was used (SAS institute, Cary, N.C., USA). Univariate analyses were performed with Pearson's $\chi^2$ test or Fisher exact test where appropriate. In the multivariate analysis, we used Akaike Information Criterion (AIC) to determine the best-fitting genetic model (dominant, co-dominant or recessive) (Akaike, 1978; Bozdogan, 1987). The model with the lowest AIC reflects the best balance of goodness-of-fit and parsimony. The genotypes of the −389 G/A promoter polymorphism were finally coded as a dummy variable according to the hypothesis for a recessive model, i.e., AA vs AG+GG genotype. The effects of this variable on the disease were estimated by multiple logistic regression models adjusted for age and APOE ε4 allele status. Extended haplotype frequencies of the different markers were estimated using the Thesias software. The objective of the thesias software is to performe haplotype-based association analysis in unrelated individuals. This program is based on the maximum likelihood model described in (Bozdogan, 1987) and is linked to the SEM algorithm (Tregouet and Tiret, 2004).

1.2. Results

Levels of gene expression were assessed in total RNA from post-mortem brain tissue of 12 controls and 12 AD patients. In the present study, the brain expression profile in each of the AD patients was compared to a pool of control samples to minimize the influence of individual variability in controls. Of the 2741 genes studied, 36 were over-expressed, and 70 under-expressed, in the brains of patients with AD compared with the pool of the controls (threefold of selection, $p<10^{-5}$).

The distribution of these genes within the different locus of interest is indicated in Table 4.

TABLE 4 number of genes exhibiting a significant differential expression in at least 6 AD brains compared with controls

| Locus | cM | Selected ORFS | Differentially expressed genes |
|---|---|---|---|
| Chr. 1 | 50 | 393 | 13 |
| Chr. 5 | 50 | 174 | 6 |
| Chr. 6 | 40 | 535 | 24 |
| Chr. 9 | 55 | 230 | 12 |
| Chr. 10 | 95 | 415 | 15 |
| Chr. 12 | 40 | 306 | 11 |
| Chr. 20 | 50 | 239 | 9 |
| Chr. 21 | 58 | 267 | 6 |
| Chr. X | 25 | 182 | 11 |

From a pool of 11 genes differentially expressed on chromosome X, the human OTC gene was selected for further analyses because no signal at all was observed for OTC on the microarrays in the control pool, whereas specific hybridisation was observed in all 12 AD samples. The inventors confirmed by RT-PCR that OTC gene was expressed in the frontal cortex in the AD patients and was not expressed in most of the control brains (only one control brain sample exhibited OTC expression under the present conditions, FIG. 1).

OTC expression at a protein level was next investigated in the brain of AD cases and controls. The endothelium of capillaries displayed immunoreactivity towards a human polyclonal anti-OTC antibody in the cortex of 6 out of 12 AD cases (FIGS. 2C and D), whereas no labelling at all was observed in all the control brains (FIG. 2B). As expected, in the control liver sections, a strong signal was observed in hepatocytes but not in the vessels and the intrahepatic bile ducts (FIG. 2A). No signal was observed when the pre-immune rabbit serum was applied instead of the anti-OTC antibody on all the samples tested (data not shown).

Following this observation, it was assessed whether the OTC gene might be a genetic determinant of AD. The inventors searched for polymorphisms within this gene using the NCBI international database (which is available on the worldwide web at ncbi.nlm.nih.gov/entrez/query.fcgi?db=Snp). Numerous mutations were described, most being responsible for OTC deficiency disease; other frequent single nucleotide polymorphisms (SNPs) were described. Six SNPs were selected within the promoter region, and 2 other non-synonymous SNPs (FIG. 4). The −146 C/T and −69 C/T SNPs could not be detected in 184 healthy old people. Furthermore, the Glu270Arg SNP exhibited a low frequency (2.3%) and consequently was excluded from further analyses. The remaining 5 selected SNPs were all in strong linkage disequilibrium (LD) (FIG. 4b). Finally, −389 G/A and −241 A/G SNPs, potentially destroying or creating a CpG motif within the OTC promoter, respectively, were investigated for association studies. Indeed, such potential modification of the promoter methylation status may be particularly relevant for the control of gene expression.

The effect of these two SNPs on the risk of developing AD was evaluated using a French case-control study comprising 583 sporadic AD cases and 639 controls. Because the OTC gene is located on the X chromosome, Hardy-Weinberg equilibrium could only be tested in females. Departure from Hardy-Weinberg equilibrium was not observed whatever the studied SNP. The genotypic distribution of the −389 G/A SNP was significantly different between AD and control populations in women (p=0.015) but not in men (Table 5). Women bearing the −389 AA genotype had an increased risk of developing AD (OR=2.3, 95% CI 1.3 to 4.1, p=0.005). This effect appeared to be independent of the APOE ε4 status and ageThe −241 A/G SNP was not associated with AD whatever the gender.

TABLE 5

Allele and genotype distributions for OTC −389 G/A, −241 A/G and Lys46Arg SNPs (a) in men and (b) in women.

| (a) Men | Allele distribution[1] (%) | | |
|---|---|---|---|
| −389 G/A | n | G | A |
| Control | 232 | 172 (0.74) | 60 (0.26) |
| AD cases | 215 | 153 (0.71) | 62 (0.29) |
| −241 A/G | n | A | G |
| Control | 232 | 167 (0.72) | 65 (0.28) |
| AD cases | 215 | 158 (0.73) | 57 (0.27) |

| (b) Women | Allele distribution (%) | | | Genotype distribution (%) | | |
|---|---|---|---|---|---|---|
| −389 G/A | n | G | A[1] | GG | AG | AA[2] |
| Control | 407 | 615 (0.76) | 199 (0.24) | 227 (0.56) | 161 (0.39) | 19 (0.05) |
| AD cases | 368 | 526 (0.71) | 210 (0.29) | 195 (0.53) | 136 (0.37) | 37 (0.10) |
| −241 A/G | n | A | G[1] | AA | AG | GG[1] |
| Control | 407 | 595 (0.73) | 219 (0.27) | 210 (0.52) | 175 (0.43) | 22 (0.05) |
| AD cases | 368 | 532 (0.72) | 204 (0.28) | 194 (0.53) | 144 (0.39) | 30 (0.08) |

[1] ns;
[2] p = 0.015

The potential combined effect of these two promoter SNPs on the risk of developing AD was next evaluated. Haplotype frequencies were computed from unphased genotypes using the Thesias software in women or directly observed in men (Table 6). The most common $G_{−389}$-$A_{−241}$ haplotype was defined as a reference. It was observed that the rare $G_{−389}$-

$G_{-241}$ haplotype was associated with decreased risk of developing AD (OR=0.3, 95% CI [0.1-0.7], p=0.001). At the opposite, the rare $A_{-389}$-$A_{-241}$ haplotype was associated with increased risk of developing the disease (OR=3.0, 95% CI [1.2-7.3], p=0.007).

TABLE 6 haplotype distribution from the −389 G/A and −241 A/G SNPs in (a) women, (b) men and (c) all the population.

| Haplotype (−389/−241) | Controls | | AD cases | | OR [95% CI] |
|---|---|---|---|---|---|
| (a) Men[1] | | | | | |
| G-A | 167 | (0.72) | 151 | (0.70) | — |
| A-A | — | | 7 | (0.03) | +∞, p = 0.006 |
| A-G | 60 | (0.26) | 59 | (0.26) | 1.1 [0.7-1.7], ns |
| G-G | 5 | (0.03) | 2 | (0.01) | 0.4 [0.1-2.6], ns |
| (b) Women[2] | | | | | |
| G-A | 587 | (0.71) | 519 | (0.70) | — |
| A-A | 8 | (0.01) | 14 | (0.02) | 2.0 [0.8-5.2°], ns |
| A-G | 195 | (0.24) | 196 | (0.27) | 1.1 [0.9-1.4], ns |
| G-G | 28 | (0.03) | 7 | (0.01) | 0.3 [0.1-0.7], p = 0.003 |
| (c) All[3] | | | | | |
| G-A | 754 | (0.72) | 670 | (0.70) | — |
| A-A | 8 | (0.01) | 21 | (0.02) | 3.0 [1.2-7.2], p = 0.007 |
| A-G | 255 | (0.24) | 255 | (0.27) | 1.1 [0.9-1.4], ns |
| G-G | 33 | (0.03) | 9 | (0.01) | 0.3 [0.1-0.7], p = 0.001 |

[1]p = 0.03;
[2]p = 0.001;
[3]p = 0.0002

In order to evaluate the potential biological relevance of the −389 G/A and −241 A/G SNPs, the inventors investigated whether these SNPs may modify the methylation status of the OTC promoter. The rare A allele of the −389 G/A SNP destroys a CpG motif. The methylation status of the cytosine residue within the CpG and CpA motifs at position −389 was determined by direct sequencing of cloned PCR products amplified from bisulfite-treated genomic DNA. Representative sequencing electrophoretograms are shown in FIG. 3.

The cytosine in the CpG motif at position −389 was systematically methylated whereas the cytosine in the CpA motif at the same position was not. They similarly assessed whether the −241 A/G SNP may modify the methylation status of the OTC promoter as the rare G allele created a CpG motif. The cytosine in the CpA motif at position −241 was systematically not methylated whereas the methylation of the cytosine in the CpG motif at the same position varied for a same individual. All these observations indicated that the methylation status of the OTC promoter may be dependent on the −389 G/A and −241 A/G SNPs. Interestingly, the rare $G_{-389}$-$G_{-241}$ haplotype was associated with a decreased risk of developing AD and may correspond to a high level of methylation of the OTC promoter conversely to the rare $A_{-389}$-$A_{-241}$ haplotype, increasing the risk of developing AD and potentially associated with a lower level of methylation.

Example 2

OTC in the Cerebrospinal Fluid is an Indicator of Brain Damages Likely to Lead to Cognitive Decline and Dementia 2.1. Materials and Methods
CSF Samples:
CSF was obtained by the "Centre de Mémoire du Service de Neurologie de l'Hôpital Salengro, CHRU de Lille" service with the enlightened and initialled assent either of the patient, or of a relative or the legal guardian. 200 μl were necessary to carry out enzymatic measures.

This study comprises 14 "Mild Cognitive Impairment (MCI)" patients, 30 patients suffering from non AD dementia (vascular dementia, mixed dementia, fronto-temporal dementia, with Lewy body etc.) and 16 suffering from probable AD.

Enzymatic Measure of the OTC Activity:
Briefly, the OTC activity is quantified via the determination of the rate of citrulline produced during a given time in the presence of its substrates in excess (FIG. 5).

The rate of citrulline is calorimetrically measured by a diacetylmonoxime-thiosemicarbazide reaction as described in Ohshita, Takeda et al. (1976). The enzymatic OTC activity was measured according to the technique described in Lee and Nussbaum, (1989), however slightly modified with the aim of being able to carry out this experiment in 96-wells plates. For each sample, two measurements, with or without added substrates, were taken and this in order to be able to measure the quantity of citrulline naturally present in the samples and to withdraw it from the total quantity of citrulline present after the OTC activity was induced by the addition of its substrates and was maintained during 30 minutes. In brief, 50 μl of CSF were added either to 140 μl of a solution containing the substrates with final concentrations of 5 mM for ornithin, 15 mM for lithium carbamyl phosphate and 270 mM for the triethanolamine or with 140 μl of distilled water. The unit was incubated during 30 minutes at 37° C. The enzymatic reaction was then stopped by the addition of 50 μl of a solution 3:1 (v/v) phosphoric acid/sulphuric acid. Finally, the colorimetric reaction making it possible to quantify the rate of citrulline present in the sample was engaged by addition of 10 μl of 2,3 butanedione 3% and was maintained at 95° C. in the dark during 15 minutes. The reading was carried out on a microplaque reader (Elx800-Biotek) at 490 nm wavelength.

Two ranges controls were carried out for each experiment, one including increasing quantities (0 to 150 nmoles/50 μl) of a commercial citrulline, the other including increasing quantities (0 to 3.10−3 unités/50 μl) of commercial OTC. For these ranges controls, two measurements were also done, in absence or in the presence of substrates, like previously described for the samples (FIGS. 7 and 8). In addition, another control was carried out by preincubating the commercial OTC enzyme with a saturating quantity of polyclonal antibodies directed against the OTC developed for this study by Proteogenix SA, France; the aim was to demonstrate that the inhibition of the enzyme by an antibody prevents the production of citrulline even in the presence of the OTC substrates (FIG. 8).

OD values were deferred on the corresponding citrulline control range in order to determine the quantity of nmoles of citrulline presents in each well. For each sample, the quantity of nmoles of citrulline measured in absence of substrates was withdrawn from the quantity of nmoles of citrulline measured in the presence of substrates, the resulting quantity representing the level of citrulline that have been produced by the OTC present in the sample during 30 minutes. It should be noted that the carryforward of this value on the OTC control range would also allow determining the level of OTC unit present in the sample. It was however chosen to express the OTC activity in moles of de novo produced citrulline/30 minutes/50 μl CSF.

2.2 Results

The results, shown in FIG. 6, indicate that the quantity of de novo produced citrulline, corresponding to the activity of the OTC measured over 30 minutes, is in average at least 10 times higher among patients presenting a MCI, a non-AD or AD dementia, compared to controls (p<0.0001).

The level of OTC activity in the CSF would hence be an effective tool to detect the existence of an objective cognitive decline, even minor, and susceptible to lead to dementia. This measurement is thus proposed as a help for the very early diagnosis of cognitive alteration and dementia.

REFERENCES

Akaike, H. (1978). A Bayesian analysis of the minimum AIC procedure. Ann Inst Statist Math 30, 9-14.

Blalock, E. M., Geddes, J. W., Chen, K. C., Porter, N. M., Markesbery, W. R., and Landfield, P. W. (2004). Incipient Alzheimer's disease: microarray correlation analyses reveal major transcriptional and tumor suppressor responses. Proc Natl Acad Sci USA 101, 2173-2178.

Bozdogan, H. (1987). Model-selection and Akaike's information criterion (AIC): the general theory and its analytical extensions. Psychometrika 52, 345-370.

Braak, H., and Braak, E. (1991). Neuropathological stageing of Alzheimer-related changes. Acta Neuropathol (Berl) 82, 239-259.

Brown, V. M., Ossadtchi, A., Khan, A. H., Cherry, S. R., Leahy, R. M., and Smith, D. J. (2002). High-throughput imaging of brain gene expression. Genome Res 12, 244-254.

Colangelo, V., Schurr, J., Ball, M. J., Pelaez, R. P., Bazan, N. G., and Lukiw, W. J. (2002). Gene expression profiling of 12633 genes in Alzheimer hippocampal CA1: transcription and neurotrophic factor down-regulation and up-regulation of apoptotic and pro-inflammatory signaling. J Neurosci Res 70, 462-473.

Cruts, M., and Van Broeckhoven, C. (1998). Molecular genetics of Alzheimer's disease. Arm Med 30, 560-565.

Delacourte, A., Sergeant, N., Champain, D., Wattez, A., Maurage, C. A., Lebert, F., Pasquier, F., and David, J. P. (2002). Nonoverlapping but synergetic tau and APP pathologies in sporadic Alzheimer's disease. Neurology 59, 398-407.

Felipo, V., and Butterworth, R. F. (2002). Neurobiology of ammonia. Prog Neurobiol 67, 259-279.

Gordon, N. (2003). Ornithine transcarbamylase deficiency: a urea cycle defect. Eur J Paediatr Neurol 7, 115-121.

Ihaka, R., and Gentlman, R. (1996). A language for data analysis and graphics. Journal of Computational and Graphical Statistics 5, 299-314.

Ishikawa, H., Matsuzawa, T., Ohashi, K., and Nagamura, Y. (2003). A novel method for measuring serum ornithine carbamoyltransferase. Ann Clin Biochem 40, 264-268.

Kamboh, M. I. (2004). Molecular genetics of late-onset Alzheimer's disease. Ann Hum Genet 68, 381-404.

Lahiri, D. K., Ge, Y. W., Maloney, B., Wavrant-De Vrieze, F., and Hardy, J. (2005). Characterization of two APP gene promoter polymorphisms that appear to influence risk of late-onset Alzheimer's disease. Neurobiol Aging 26, 1329-1341.

Lambert, J. C., Araria-Goumidi, L., Myllykangas, L., Ellis, C., Wang, J. C., Bullido, M. J., Harris, J. M., Artiga, M. J., Hernandez, D., Kwon, J. M., et al. (2002). Contribution of APOE promoter polymorphisms to Alzheimer's disease risk. Neurology 59, 59-66.

Lambert, J. C., Testa, E., Cognat, V., Soula, J., Hot, D., Lemoine, Y., Gaypay, G., and Amouyel, P. (2003). Relevance and limitations of public databases for microarray design: a critical approach to gene predictions. Pharmacogenomics J 3, 235-241.

Lee, J. T., and Nussbaum, R. L. (1989). An arginine to glutamine mutation in residue 109 of human ornithine transcarbamylase completely abolishes enzymatic activity in Cos1 cells. J Clin Invest 84, 1762-1766.

Li, Y. J., Oliveira, S. A., Xu, P., Martin, E. R., Stenger, J. E., Scherzer, C. R., Hauser, M. A., Scott, W. K., Small, G. W., Nance, M. A., et al. (2003). Glutathione S-transferase omega-1 modifies age-at-onset of Alzheimer disease and Parkinson disease. Hum Mol Genet 12, 3259-3267.

Lönnstedt, I., and Speed, T. p. (2002). Replicated Microarray Data. Statistica Sinica 12, 31-46.

Loring, J. F., Wen, X., Lee, J. M., Seilhamer, J., and Somogyi, R. (2001). A gene expression profile of Alzheimer's disease. DNA Cell Biol 20, 683-695.

Mirra, S. S., Heyman, A., McKeel, D., Sumi, S. M., Crain, B. J., Brownlee, L. M., Vogel, F. S., Hughes, J. P., van Belle, G., and Berg, L. (1991). The Consortium to Establish a Registry for Alzheimer's Disease (CERAD). Part II. Standardization of the neuropathologic assessment of Alzheimer's disease. Neurology 41, 479-486.

Murayama, H., Igarashi, M., Mori, M., Fukuda, Y., Ikemoto, M., and Nagata, A. (2006). A sensitive ELISA for serum ornithine carbamoyltransferase utilizing the enhancement of immunoreactivity at alkaline pH. Clin Chim Acta.

Ohshita, M., Takeda, H., Kamiyama, Y., Ozawa, K., and Honjo, I. (1976). A direct method for the estimation of ornithine carbamoyltransferase activity in serum. Clin Chim Acta 67, 145-152.

Riazanskaia, N., Lukiw, W. J., Grigorenko, A., Korovaitseva, G., Dvoryanchikov, G., Moliaka, Y., Nicolaou, M., Farrer, L., Bazan, N. G., and Rogaev, E. (2002). Regulatory region variability in the human presenilin-2 (PSEN2) gene: potential contribution to the gene activity and risk for AD. Mol Psychiatry 7, 891-898.

Roberts, S. B., MacLean, C. J., Neale, M. C., Eaves, L. J., and Kendler, K. S. (1999). Replication of linkage studies of complex traits: an examination of variation in location estimates. Am J Hum Genet 65, 876-884.

Smyth, G. K., Yang, Y. H., and Speed, T. (2003). Statistical issues in cDNA microarray data analysis. Methods Mol Biol 224, 111-136.

Theuns, J., Del-Favero, J., Dermaut, B., van Duijn, C. M., Backhovens, H., Van den Broeck, M. V., Serneels, S., Corsmit, E., Van Broeckhoven, C. V., and Cruts, M. (2000). Genetic variability in the regulatory region of presenilin 1 associated with risk for Alzheimer's disease and variable expression. Hum Mol Genet 9, 325-331.

Tregouet, D. A., and Tiret, L. (2004). Cox proportional hazards survival regression in haplotype-based association analysis using the Stochastic-EM algorithm. Eur J Hum Genet 12, 971-974.

Wiesinger, H. (2001). Arginine metabolism and the synthesis of nitric oxide in the nervous system. Prog Neurobiol 64, 365-391.

Yang, Y. H., Dudoit, S., Luu, P., Lin, D. M., Peng, V., Ngai, J., and Speed, T. P. (2002). Normalization for cDNA microarray data: a robust composite method addressing single and multiple slide systematic variation. Nucleic Acids Res 30, e15.

The invention claimed is:

1. A method for diagnosing Alzheimer's disease in a deceased individual, comprising a step of labelling a brain biopsy from said individual, with an anti-OTC antibody, wherein detection of ornithine transcarbamylase in cerebrovascular endothelial cells of said biopsy is indicative of Alzheimer's disease.

2. The method of claim 1, wherein said antibody is a monoclonal or polyclonal antibody obtained against a polypeptide with the amino acid sequence MKTAKVAASDWTFLHCLPRK (SEQ ID No: 17).

3. A method of aiding in diagnosis of Alzheimer's disease, non-Alzeimer's disease dementia or mild cognitive impairment in an individual, said method comprising a step of measuring ornithine transcarbamylase (OTC) level and/or activity in a sample of cerebrospinal fluid from said individual, wherein a level or activity of ornithine transcarbamylase which is higher than the level or activity which is statistically observed in healthy subjects is indicative of Alzheimer's disease, non-Alzeimer's disease dementia or mild cognitive impairment.

4. The method of claim 3, wherein the method is aiding in diagnosis of Alzheimer's disease.

5. The method according to claim 3, wherein the measuring of ornithine transcarbamylase (OTC) in said sample of cerebrospinal fluid is performed by measuring the OTC activity.

6. The method of claim 3, wherein the OTC activity is measured by measuring the production of citrulline after addition of carbamyl phosphate and ornithine to said sample.

7. The method of claim 6, wherein the OTC activity is measured by colorimetrically measuring citrulline production.

8. The method according to claim 3, wherein the OTC activity is measured by measuring the production of glutamate after addition of ornithine-ketoacid aminotransferase (OKT), Delta(1)-pyrroline-5-carboxylate dehydrogenase (P5CDH) and glutamate dehydrogenase (GDH) to said sample.

9. The method according to claim 3, wherein the measuring of ornithine transcarbamylase (OTC) in said sample of cerebrospinal fluid is performed by immunoassay with a monoclonal or polyclonal antibody directed against OTC.

10. The method of claim 9, wherein said antibody is a monoclonal or polyclonal antibody obtained against a polypeptide with the amino acid sequence MKTAKVAASDWTFLHCLPRK (SEQ ID No: 17).

* * * * *

SEQUENCE LISTING

<160> NUMBER OF SEQ ID NOS: 28

<210> SEQ ID NO 1
<211> LENGTH: 21
<212> TYPE: DNA
<213> ORGANISM: Artificial
<220> FEATURE:
<223> OTHER INFORMATION: Synthetic primer

<400> SEQUENCE: 1
ctcctgaggt ggccatagtt g                                          21

<210> SEQ ID NO 2
<211> LENGTH: 21
<212> TYPE: DNA
<213> ORGANISM: Artificial
<220> FEATURE:
<223> OTHER INFORMATION: Synthetic primer

<400> SEQUENCE: 2
ccaacatggt gaatccccgt c                                          21

<210> SEQ ID NO 3
<211> LENGTH: 20
<212> TYPE: DNA
<213> ORGANISM: Artificial
<220> FEATURE:
<223> OTHER INFORMATION: Synthetic primer

<400> SEQUENCE: 3
atctgggctc actgcaacct                                            20

<210> SEQ ID NO 4
<211> LENGTH: 20
<212> TYPE: DNA
<213> ORGANISM: Artificial
<220> FEATURE:
<223> OTHER INFORMATION: Synthetic primer

<400> SEQUENCE: 4
gagaccagcc tggccaacag                                            20

<210> SEQ ID NO 5
<211> LENGTH: 21
<212> TYPE: DNA
<213> ORGANISM: Artificial
<220> FEATURE:
<223> OTHER INFORMATION: Synthetic primer

<400> SEQUENCE: 5
gtggagacgg ggattcacca t                                          21

<210> SEQ ID NO 6
<211> LENGTH: 20
<212> TYPE: DNA
<213> ORGANISM: Artificial
<220> FEATURE:
<223> OTHER INFORMATION: Synthetic primer

<400> SEQUENCE: 6
gggcacggtg gctcacgact                                            20

<210> SEQ ID NO 7
<211> LENGTH: 20
<212> TYPE: DNA

```
<213> ORGANISM: Artificial
<220> FEATURE:
<223> OTHER INFORMATION: Synthetic primer

<400> SEQUENCE: 7
gtgtggacaa ccactacaaa                                               20

<210> SEQ ID NO 8
<211> LENGTH: 20
<212> TYPE: DNA
<213> ORGANISM: Artificial
<220> FEATURE:
<223> OTHER INFORMATION: Synthetic primer

<400> SEQUENCE: 8
tgttacatac ctctcctttc                                               20

<210> SEQ ID NO 9
<211> LENGTH: 20
<212> TYPE: DNA
<213> ORGANISM: Artificial
<220> FEATURE:
<223> OTHER INFORMATION: Synthetic primer

<400> SEQUENCE: 9
atggtaccaa gctgttgctg                                               20

<210> SEQ ID NO 10
<211> LENGTH: 20
<212> TYPE: DNA
<213> ORGANISM: Artificial
<220> FEATURE:
<223> OTHER INFORMATION: Synthetic primer

<400> SEQUENCE: 10 cgcttttttct tctcctcgtc                                              20

<210> SEQ ID NO 11
<211> LENGTH: 20
<212> TYPE: DNA
<213> ORGANISM: Artificial
<220> FEATURE:
<223> OTHER INFORMATION: Synthetic primer

<400> SEQUENCE: 11
ataaatgtga agttgtagat                                               20

<210> SEQ ID NO 12
<211> LENGTH: 21
<212> TYPE: DNA
<213> ORGANISM: Artificial
<220> FEATURE:
<223> OTHER INFORMATION: Synthetic primer

<400> SEQUENCE: 12
taattaccta ttaattctaa c                                             21

<210> SEQ ID NO 13
<211> LENGTH: 20
<212> TYPE: DNA
<213> ORGANISM: Artificial
<220> FEATURE:
<223> OTHER INFORMATION: Synthetic primer

<400> SEQUENCE: 13
gaataggttg ttaggggaag                                               20
```

```
<210> SEQ ID NO 14
<211> LENGTH: 20
<212> TYPE: DNA
<213> ORGANISM: Artificial
<220> FEATURE:
<223> OTHER INFORMATION: Synthetic primer

<400> SEQUENCE: 14
ataaatgtga agttgtagat                                               20

<210> SEQ ID NO 15
<211> LENGTH: 26
<212> TYPE: DNA
<213> ORGANISM: Artificial
<220> FEATURE:
<223> OTHER INFORMATION: Synthetic primer

<400> SEQUENCE: 15
tgggtttatt gtaatttttg tttttt                                        26

<210> SEQ ID NO 16
<211> LENGTH: 26
<212> TYPE: DNA
<213> ORGANISM: Artificial
<220> FEATURE:
<223> OTHER INFORMATION: Synthetic primer

<400> SEQUENCE: 16
ctaaccaaca taataaatcc cccatc                                        26

<210> SEQ ID NO 17
<211> LENGTH: 20
<212> TYPE: PRT
<213> ORGANISM: Artificial
<220> FEATURE:
<223> OTHER INFORMATION: Synthetic polypeptide

<400> SEQUENCE: 17

Met Lys Thr Ala Lys Val Ala Ala Ser Asp Trp Thr Phe Leu His Cys
1               5                   10                  15

Leu Pro Arg Lys
            20

<210> SEQ ID NO 18
<211> LENGTH: 20
<212> TYPE: DNA
<213> ORGANISM: Artificial
<220> FEATURE:
<223> OTHER INFORMATION: Synthetic primer

<400> SEQUENCE: 18
aagacctggc atcaggctcc                                               20

<210> SEQ ID NO 19
<211> LENGTH: 20
<212> TYPE: DNA
<213> ORGANISM: Artificial
<220> FEATURE:
<223> OTHER INFORMATION: Synthetic primer

<400> SEQUENCE: 19
tggtagccag ccagtggttg                                               20

<210> SEQ ID NO 20
<211> LENGTH: 20
<212> TYPE: DNA
```

```
<213> ORGANISM: Artificial
<220> FEATURE:
<223> OTHER INFORMATION: Synthetic primer

<400> SEQUENCE: 20
tcccaattat caatgggctg                                                 20

<210> SEQ ID NO 21
<211> LENGTH: 21
<212> TYPE: DNA
<213> ORGANISM: Artificial
<220> FEATURE:
<223> OTHER INFORMATION: Synthetic primer

<400> SEQUENCE: 21
catgcttatc caaagtgtct g                                               21

<210> SEQ ID NO 22
<211> LENGTH: 20
<212> TYPE: DNA
<213> ORGANISM: Artificial
<220> FEATURE:
<223> OTHER INFORMATION: Synthetic primer

<400> SEQUENCE: 22
cagtcctgct ctgccgcctg                                                 20

<210> SEQ ID NO 23
<211> LENGTH: 21
<212> TYPE: DNA
<213> ORGANISM: Artificial
<220> FEATURE:
<223> OTHER INFORMATION: Synthetic primer

<400> SEQUENCE: 23
ccggccagat gaactcctcc a                                               21

<210> SEQ ID NO 24
<211> LENGTH: 18
<212> TYPE: DNA
<213> ORGANISM: Artificial
<220> FEATURE:
<223> OTHER INFORMATION: Synthetic primer

<400> SEQUENCE: 24
gaggaaccgc ccaacatg                                                   18

<210> SEQ ID NO 25
<211> LENGTH: 20
<212> TYPE: DNA
<213> ORGANISM: Artificial
<220> FEATURE:
<223> OTHER INFORMATION: Synthetic primer

<400> SEQUENCE: 25
ccaccttgtc taggccatgg                                                 20

<210> SEQ ID NO 26
<211> LENGTH: 20
<212> TYPE: DNA
<213> ORGANISM: Artificial
<220> FEATURE:
<223> OTHER INFORMATION: Synthetic primer

<400> SEQUENCE: 26
cctacagtat tgagaaaggc                                                 20
```

```
<210> SEQ ID NO 27
<211> LENGTH: 20
<212> TYPE: DNA
<213> ORGANISM: Artificial
<220> FEATURE:
<223> OTHER INFORMATION: Synthetic primer

<400> SEQUENCE: 27
ttccacttgt ggttgtcagt                                              20

<210> SEQ ID NO 28
<211> LENGTH: 20
<212> TYPE: PRT
<213> ORGANISM: Homo sapiens

<400> SEQUENCE: 28

Met Lys Thr Ala Lys Val Ala Ala Ser Asp Trp Thr Phe Leu His Cys
1               5                   10                  15

Leu Pro Arg Lys
            20
```